(12) United States Patent
Lee et al.

(10) Patent No.: US 7,553,949 B2
(45) Date of Patent: Jun. 30, 2009

(54) REVERSIBLE TERMINATOR NUCLEOTIDES AND METHODS OF USE

(75) Inventors: Linda G. Lee, Palo Alto, CA (US); Gerald Zon, San Carlos, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 11/763,405

(22) Filed: Jun. 14, 2007

(65) Prior Publication Data

US 2008/0050780 A1 Feb. 28, 2008

Related U.S. Application Data

(60) Provisional application No. 60/818,009, filed on Jun. 30, 2006.

(51) Int. Cl.
*C07H 21/00* (2006.01)
*C07H 21/02* (2006.01)
*C12Q 1/68* (2006.01)
*C12P 19/34* (2006.01)

(52) U.S. Cl. .................... 536/23.1; 536/24.3; 536/26.6

(58) Field of Classification Search ............... 536/23.1, 536/24.3, 26.6; 435/6, 91.1
See application file for complete search history.

(56) References Cited

U.S. PATENT DOCUMENTS 7,057,026 B2 * 6/2006 Barnes et al. ............. 536/23.1

* cited by examiner

*Primary Examiner*—Jezia Riley (57) ABSTRACT

Disclosed herein a reversible terminator nucleotides and methods of use.

6 Claims, 3 Drawing Sheets

REVERSIBLE TERMINATOR NUCLEOTIDES AND METHODS OF USE

1. CROSS REFERENCE TO RELATED APPLICATION

This application claims benefit under 35 U.S.C. § 119(e) to provisional application No. 60/818,009, filed Jun. 30, 2006, the disclosure of which is incorporated herein by reference.

2. INTRODUCTION

Methods of polynucleotide sequencing that employ reversible terminator nucleotides typically involve multiple steps to identify a single base and to regenerate a 3' terminus of the sequencing primer which is required permit identification of each succeeding base of the polynucleotide. These steps typically include incorporation of a reversible terminator at the 3' terminus of the primer, washing away the unincorporated reversible terminators and other sequencing reagents, detection of the label attached to the incorporated reversible terminator, removal of the label from the incorporated terminator, and removal of blocking group from the reversible terminator. Therefore, current methods of polynucleotide sequencing using reversible terminators are time-consuming, labor intensive, and have a high-cost associated with the identification of each base. Therefore, there is a need in the art for reversible terminator nucleotides and methods of use that reduce the number of steps required for the identification of each base of a polynucleotide.

4. DETAILED DESCRIPTION

This section should describe in detail the various different embodiments of the invention(s). It should use headings to help organize the various component parts of the invention(s).

Disclosed herein are compositions and methods for sequencing polynucleotides, including single-molecule sequencing. The compositions disclosed herein include reversible terminator nucleotides that can be incorporated at the 3' terminus of a polynucleotide by a polymerase in a template dependent/directed manner. In some embodiments, the reversible terminator nucleotides generally include a hydroxyl group at the 3'-position of a sugar moiety, a blocking group at the 2'-position of the sugar moiety, and a label attached to the base. Upon incorporation of a reversible terminator nucleotide, the blocking group renders the polynucleotide non-extendible by the polymerase. In some embodiments, the incorporated reversible terminators also are generally resistant to 3'-5' exonucleases or "proofreading activities" of polymerases.

4.2 Definitions

As used herein, the following terms are intended to have the following meanings:

"Nucleoside" refers to a compound consisting of a purine, deazapurine, or pyrimidine nucleoside base, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose. When the nucleoside base is purine or 7-deazapurine, the pentose is attached at the 9-position of the purine or deazapurine, and when the nucleoside base is pyrimidine, the pentose is attached at the 1-position of the pyrimidine (see, e.g., Kornberg and Baker, *DNA Replication,* 2nd Ed. (Freeman 1992)). The term "nucleotide" as used herein refers to a phosphate ester of a nucleoside, e.g., a mono-, a di-, or a triphosphate ester, wherein the most common site of esterification is the hydroxyl group attached to the C-5 position of the pentose. "Nucleotide 5'-triphosphate" refers to a nucleotide with a triphosphate ester group at the 5' position. The term "nucleoside/tide" as used herein refers to a set of compounds including both nucleosides and/or nucleotides.

"Nucleobase polymer or oligomer" refers to two or more nucleobases connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Polynucleotide or oligonucleotide" refers to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

In some embodiments, a nucleobase polymer is an polynucleotide analog or an oligonucleotide analog. By "polynucleotide analog or oligonucleotide analog" is meant nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani, 1995, *Chem. & Eng. News* 4-5:1153; Dempey et al., 1995, *J. Am. Chem. Soc.* 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g., Elayadi et al., 2002, *Biochemistry* 41:9973-9981; Koshkin et al., 1998, *J. Am. Chem. Soc.* 120: 13252-3; Koshkin et al., 1998, *Tetrahedron Letters,* 39:4381-4384; Jumar et al., 1998, *Bioorganic & Medicinal Chemistry Letters* 8:2219-2222; Singh and Wengel, 1998, *Chem. Commun.,* 12:1247-1248; WO 00/56746; WO 02/28875; and, WO 01/48190.

In some embodiments, a nucleobase polymer is a polynucleotide mimic or oligonucleotide mimic. "Polynucleotide mimic or oligonucleotide mimic" refers to a nucleobase polymer or oligomer in which one or more of the backbone sugar-phosphate linkages is replaced with a sugar-phosphate analog. Such mimics are capable of hybridizing to complementary polynucleotides or oligonucleotides, or polynucleotide or oligonucleotide analogs or to other polynucleotide or oligonucleotide mimics, and may include backbones comprising one or more of the following linkages: positively charged polyamide backbone with alkylamine side chains as described in U.S. Pat. Nos. 5,786,461, 5,766,855, 5,719,262, 5,539,082 and WO 98/03542 (see also, Haaima et al., 1996, *Angewandte Chemie Int'l Ed.* in English 35:1939-1942; Lesnick et al., 1997, *Nucleotid.* 16:1775-1779; D'Costa et al., 1999, *Org. Lett.* 1:1513-1516; Nielsen, 1999, *Curr. Opin. Biotechnol.* 10:71-75); uncharged polyamide backbones as described in WO 92/20702 and U.S. Pat. No. 5,539,082; uncharged morpholino-phosphoramidate backbones as described in U.S. Pat. Nos. 5,698,685, 5,470,974, 5,378,841, and 5,185,144 (see also, Wages et al., 1997, *BioTechniques* 23:1116-1121); peptide-based nucleic acid mimic backbones (see, e.g., U.S. Pat. No. 5,698,685); carbamate backbones (see, e.g., Stirchak and Summerton, 1987, *J. Org. Chem.* 52:4202); amide backbones (see, e.g., Lebreton, 1994, *Synlett.* February, 1994:137); methylhydroxyl amine backbones (see, e.g., Vasseur et al., 1992, *J. Am. Chem. Soc.* 114:4006); 3'-thioformacetal backbones (see, e.g., Jones et al., 1993, J. Org. Chem. 58:2983) and sulfamate backbones (see, e.g., U.S. Pat. No. 5,470,967). All of the preceding references are herein incorporated by reference.

"Peptide nucleic acid" or "PNA" refers to poly- or oligo-nucleotide mimics in which the nucleobases are connected by amino linkages (uncharged polyamide backbone) such as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. The term "peptide nucleic acid" or "PNA" shall also apply to any oligomer or polymer comprising two or more subunits of those polynucleotide mimics described in the following publications: Lagriffoul et al, 1994, *Bioorganic & Medicinal Chemistry Letters,* 4:1081-1082; Petersen et al., 1996, *Bioorganic & Medicinal Chemistry Letters,* 6:793-796; Diderichsen et al., 1996, *Tett. Lett.* 37:475-478; Fujii et al., 1997, *Bioorg. Med. Chem. Lett.* 7:637-627; Jordan et al., 1997, *Bioorg. Med. Chem. Lett.* 7:687-690; Krotz et al., 1995, *Tett. Lett.* 36:6941-6944; Lagriffoul et al., 1994, *Bioorg. Med. Chem. Lett.* 4:1081-1082; Diederichsen, 1997, *Bioorg. Med. Chem.* 25 Letters, 7:1743-1746; Lowe et al., 1997, *J. Chem. Soc.* Perkin Trans. 1, 1:539-546; Lowe et al, 1997, *J. Chem. Soc.* Perkin Trans. 11:547-554; Lowe et al., 1997, *I. Chem. Soc.* Perkin Trans. 11:555-560; Howarth et al., 1997, *I. Org. Chem.* 62:5441-5450; Altmann et al., 1997, *Bioorg. Med. Chem. Lett.,* 7:1119-1122; Diederichsen, 1998, *Bioorg. Med. Chem. Lett.,* 8:165-168; Diederichsen et al., 1998, *Angew. Chem.* mt. Ed., 37:302-305; Cantin et al., 1997, *Tett. Lett.,* 38:4211-4214; Ciapetti et al., 1997, *Tetrahedron,* 53:1167-1176; Lagriffoule et al., 1997, *Chem. Eur.* 1. 3:912-919; Kumar et al., 2001, *Organic Letters* 3(9):1269-1272; and the Peptide-Based Nucleic Acid Mimics (PENAMs) of Shah et al. as disclosed in WO 96/04000.

Some examples of PNAs are those in which the nucleobases are attached to an N-(2-aminoethyl)-glycine backbone, i.e., a peptide-like, amide-linked unit (see, e.g., U.S. Pat. No. 5,719,262; Buchardt et al., 1992, WO 92/20702; Nielsen et al., 1991, *Science* 254:1497-1500).

In some embodiments, a nucleobase polymer is a chimeric oligonucleotide. By "chimeric oligonucleotide" is meant a nucleobase polymer or oligomer comprising a plurality of different polynucleotides, polynucleotide analogs and polynucleotide mimics. For example a chimeric oligo may comprise a sequence of DNA linked to a sequence of RNA. Other examples of chimeric oligonucleotides include a sequence of DNA linked to a sequence of PNA, and a sequence of RNA linked to a sequence of PNA.

In some embodiments, a nucleobase polymer is a chimeric oligonucleotide. By "chimeric oligonucleotide" is meant a nucleobase polymer or oligomer comprising a plurality of different polynucleotides, polynucleotide analogs and polynucleotide mimics. For example a chimeric oligo may comprise a sequence of DNA linked to a sequence of RNA. Other examples of chimeric oligonucleotides include a sequence of DNA linked to a sequence of PNA, and a sequence of RNA linked to a sequence of PNA.

In some embodiments, various components of the disclosed methods, including but not limited to primers, reversible terminator nucleotides, and other reaction compartments, can comprise a detectable moiety. "Detectable moiety," "detection moiety" or "label" refer to a moiety that renders a molecule to which it is attached detectable or identifiable using known detection systems (e.g., spectroscopic, radioactive, enzymatic, chemical, photochemical, biochemical, immunochemical, chromatographic, physical (e.g., sedimentation, centrifugation, density), electrophoretic, gravimetric, or magnetic systems). Non-limiting examples of labels include quantum dots, isotopic labels (e.g., radioactive or heavy isotopes), magnetic labels; spin labels, electric labels; thermal labels; colored labels (e.g., chromophores), luminescent labels (e.g., fluorescers, chemiluminescers), enzyme labels (e.g., horseradish peroxidase, alkaline phosphatase, luciferase, β-galactosidase)(Ichiki, et al., 1993, *J. Immunol.* 150(12):5408-5417; Nolan, et al., 1988, *Proc. Natl. Acad. Sci.* USA 85(8):2603-2607)), antibody labels, and chemically modifiable labels. In addition, in some embodiments, such labels include components of ligand-binding partner pairs (e.g., antigen-antibody (including single-chain antibodies and antibody fragments, e.g., FAb, F(ab)'$_2$, Fab', Fv, etc. (*Fundamental Immunology* 47-105 (William E. Paul ed., 5$^{th}$ ed., Lippincott Williams & Wilkins 2003)), hormone-receptor binding, neurotransmitter-receptor binding, polymerase-promoter binding, substrate-enzyme binding, inhibitor-enzyme binding (e.g., sulforhodamine-valyl-alanyl-aspartyl-fluoromethylketone (SR-VAD-FMK-caspase(s) binding), allosteric effector-enzyme binding, biotin-streptavidin binding, digoxin-antidigoxin binding, carbohydrate-lectin binding, Annexin V-phosphatidylserine binding (Andree et al., 1990, *J. Biol. Chem.* 265(9):4923-8; van Heerde et al., 1995, *Thromb. Haemost.* 73(2):172-9; Tait et al., 1989, *J. Biol. Chem.* 264(14):7944-9), nucleic acid annealing or hybridization, or a molecule that donates or accepts a pair of electrons to form a coordinate covalent bond with the central metal atom of a coordination complex. In various exemplary embodiments the dissociation constant of the binding ligand can be less than about $10^{-4}$-$10^{-6}$ M$^{-1}$, less than about $10^{-5}$ to $10^{-9}$ M$^{-1}$, or less than about $10^{-7}$-$10^{-9}$ M$^{-1}$.

"Fluorescent label," "fluorescent moiety," and "fluorophore" refer to a molecule that may be detected via its inherent fluorescent properties. Examples of suitable fluorescent labels include, but are not limited to, fluorescein, rhodamine, tetramethylrhodamine, eosin, erythrosin, coumarin, methyl-coumarins, pyrene, Malachite Green, stilbene, Lucifer Yellow, Cascade BlueJ, Texas Red, IAEDANS, EDANS, BODIPY FL, LC Red 640, phycoerythrin, LC Red 705, Oregon green, Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE), FITC, Rhodamine, Texas Red (Pierce, Rockford, Ill.), Cy5, Cy5.5, Cy7 (Amersham Life Science, Pittsburgh, Pa.) and tandem conjugates, such as but not limited to, Cy5PE, Cy5.5PE, Cy7PE, Cy5.5APC, Cy7APC. In some embodiments, suitable fluorescent labels also include, but are not limited to, green fluorescent protein (GFP; Chalfie, et al., 1994, Science 263(5148):802-805), EGFP (Clontech Laboratories, Inc., Palo Alto, Calif.), blue fluorescent protein (BFP; Quantum Biotechnologies, Inc. Montreal, Canada; Heim et al, 1996, Curr. Biol. 6:178-182; Stauber, 1998, Biotechniques 24(3):462-471; ), enhanced yellow fluorescent protein (EYFP; Clontech Laboratories, Inc., Palo Alto, Calif.), and renilla (WO 92/15673; WO 95/07463; WO 98/14605; WO 98/26277; WO 99/49019; U.S. Pat. Nos. 5,292,658, 5,418,155, 5,683,888, 5,741,668, 5,777,079, 5,804,387, 5,874,304, 5,876,995, and 5,925,558). Further examples of fluorescent labels are found in Haugland, *Handbook of Fluorescent Probes and Research*, 9$^{th}$ Edition, Molecule Probes, Inc. Eugene, Oreg. (ISBN 0-9710636-0-5).

By "microparticle", "microsphere", "microbead", "bead" and grammatical equivalents herein are meant a small discrete synthetic particle. As known in the art, the composition of beads can vary depending on the type of assay in which they are used and, therefore, selecting a microbead composition is within the abilities of the practitioner. Suitable bead compositions include those used in peptide, nucleic acid and organic synthesis, including, but not limited to, plastics, ceramics, glass, polystyrene, methylstyrene, acrylic polymers, paramagnetic materials (U.S. Pat. Nos. 4,358,388, 4,654,267, 4,774,265, 5,320,944, 5,356,713), thoria sol, carbon graphite, titanium dioxide, latex or cross-linked dextrans such as Sepharose, agarose, cellulose, carboxymethyl cellulose, hydroxyethyl cellulose, proteinaceous polymer, nylon, globulin, DNA, cross-linked micelles and Teflon may all be used (see, e.g., *Microsphere Detection Guide* from Bangs Laboratories, Fishers, Ind.), Beads are also commercially available from, for example, Bio-Rad Laboratories (Richmond, Calif.), LKB (Sweden), Pharmacia (Piscataway, N.J.), IBF (France), Dynal Inc. (Great Neck, N.Y.). In some embodiments, beads may contain a cross-linking agent, such as, but not limited to divinyl benzene, ethylene glycol dimethacrylate, trimethylol propane trimethacrylate, N,N'methylene-bis-acrylamide, adipic acid, sebacic acid, succinic acid, citric acid, 1,2,3,4-butanetetracarboxylic acid, or 1,10 decanedicarboxylic acid or other functionally equivalent agents known in the art. In various exemplary embodiments, beads can be spherical, non-spherical, egg-shaped, irregularly shaped, and the like. The average diameter of a microparticle can be selected at the discretion of the practitioner. However, generally the average diameter of microparticle can range from nanometers (e.g. about 100 nm) to millimeters (e.g. about 1 mm) with beads from about 0.2 μm to about 200 μm being preferred, and from about 0.5 to about 10 μm being particularly preferred, although in some embodiments smaller or larger beads may be used, as described below.

In some embodiments a microparticle can be porous, thus increasing the surface area available for attachment to another molecule, moiety, or compound (e.g., a primer). Thus, microparticles may have additional surface functional groups to facilitate attachment and/or bonding. These groups may include carboxylates, esters, alcohols, carbamides, aldehydes, amines, sulfur oxides, nitrogen oxides, or halides.

Methods of attaching another molecule or moiety to a bead are known in the art (see, e.g., U.S. Pat. Nos. 6,268,222, 6,649,414). In some embodiments, a microparticle can further comprise a label.

An "extended polynucleotide" refers to a polynucleotide to which one or more additional nucleotides have been added or otherwise incorporated (e.g., covalently bonded to).

A "template polynucleotide" refers to a polynucleotide to which a primer can hybridize and be extended. Accordingly, template polynucleotides include subsequences that are at least partially complementary to a primer. Template polynucleotides can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template polynucleotides optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto. As used herein, a "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

Polynucleotides are "extended" or "elongated" when additional nucleotides (or other analogous molecules, e.g., reversible terminator nucleotides) are incorporated into the nucleic acids. For example, a polynucleotide is optionally extended by a nucleotide incorporating polymerase that typically adds nucleotides at the 3' terminal end of a polynucleotide.

An "extendible polynucleotide" refers to a nucleotide to which at least one other nucleotide can be added or covalently bonded, e.g., in a reaction catalyzed by a polymerase once the extendible polynucleotide is incorporated. An extendible polynucleotide is typically extended by adding another nucleotide at a 3'-position of the sugar moiety.

A "non-extendible" nucleotide refers to a nucleotide, which upon incorporation into a polynucleotide at least substantially inhibits further extension of the polynucleotide.

"Parallel reaction" as used herein refers to a reaction comprising a plurality of discrete regions suitable for performing a plurality of reactions simultaneously. Virtually any number of polynucleotides can analyzed in parallel. For example, in various exemplary embodiments, hundreds, thousands, hundreds of thousands, millions, and even greater numbers of polynucleotides can be analyzed in parallel by the disclosed methods. In various exemplary embodiments the numbers of polynucleotides analyzed in parallel can be at least 2, 100, 500, 1000, 10000, 50000, 100000, 300000, 500000, or 1000000, and even greater.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety (e.g., a moiety comprising a sugar ring or an analog thereof), and one or more phosphate groups.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane, cycloheptane, cyclohexene, and the like.

An "alkyl group" refers to a linear, branched, or cyclic saturated hydrocarbon moiety and includes all positional isomers, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, and the like. An alkenyl group typically comprises about 1-20 carbon atoms and more typically comprises about 2-15 carbon atoms. Alkenyl groups can be substituted or unsubstituted.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. An alkynyl group typically comprises about 1-20 carbon atoms and more typically comprises about 2-15 carbon atoms. Alkynyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

A "halo group" refers to a group that comprises a halogen atom, such as F, Cl, Br, or I.

An "aryl group" refers to a substituent group of atoms or moiety that is derived from an aromatic compound. Exemplary aryl groups include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties.

An "ether group" refers to a linear, branched, or cyclic moiety that comprises two carbon atoms attached to a single oxygen atom. Exemplary ether groups include, e.g., methoxymethyl, methoxyethyl, methoxypropyl, ethoxyethyl, and the like.

A "thioether group" refers to a linear, branched, or cyclic moiety that comprises two carbon atoms attached to a single sulfur atom and includes, e.g., methylthiomethyl, methylthioethyl, methylthiopropyl, and the like.

An "alkylamine group" refers to an amino group that comprises at least one alkyl group.

An "alkenylamine group" refers to an amino group that comprises at least one alkenyl group.

An "alkynylamine group" refers to an amino group that comprises at least one alkynyl group.

An "ester group" refers to a class of organic compounds that includes the general formula RCOOR', where R and R' are independently selected from an alkyl group, an alkenyl group, an alkynyl group, an aryl group, or combinations thereof.

A "polyaminoacid" refers to compound or group that comprises two or more amino acid residues. Exemplary polyaminoacids include peptides, polypeptides, proteins, and the like.

An "aldehyde group" refers to an organic group that includes the formula CHO.

An "alcohol group" refers to an organic group that includes at least one hydroxy group.

A "silyl group" refers to a class of compounds that includes the general formula SiRR'R", where R, R', and R" are independently an H, an alkyl group, an alkenyl group, an alkynyl group, an aryl group, or a combination of such groups.

A "phosphate analog" refers to a moiety that can be cleaved by a phosphatase, such as, an alkaline phosphatase.

A "sequence" of a polynucleotide refers to the order and identity of nucleotides in the nucleic acid. A sequence is typically read in the 5' to 3' direction.

"Attached" refers to interactions including, but not limited to, covalent bonding, ionic bonding, chemisorption, physisorption, and combinations thereof.

A "linker" or "spacer" refers to a chemical moiety that covalently or non-covalently (e.g., ionically, etc.) attaches a compound or substituent group to, e.g., a solid support, another compound or group, or the like. For example, a linker optionally attaches a label (e.g., a fluorescent dye, a radioisotope, etc.) to a 2'-terminator nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) Nucleic Acids Res. 24(14):2793, Shchepino et al. (2001) Nucleosides, Nucleotides, & Nucleic Acids 20:369, Doronina et al (2001) Nucleosides, Nucleotides, & Nucleic Acids 20:1007, Trawick et al. (2001) Bioconjugate Chem. 12:900, Olejnik et al. (1998) Methods in Enzymology 291:135, Pljevaljcic et al. (2003) J. Am. Chem. Soc. 125(12): 3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "modified" enzyme refers to an enzyme comprising a sequence in which at least one amino acid differs from a reference sequence, such as a native or wild-type form of the enzyme or another modified form of the enzyme, e.g., when the two sequences are aligned for maximum identity. Exemplary modifications include monomer insertions, deletions, and substitutions. The modified enzymes (e.g., polymerases) can be created by various diversity generating methods. Although essentially any method can be used to produce a modified enzyme, certain exemplary techniques include recombining (e.g., via recursive recombination, synthetic recombination, or the like) two or more nucleic acids encoding one or more parental enzymes, or by mutating one or more nucleic acids that encode enzymes, e.g., using recursive ensemble mutagenesis, cassette mutagenesis, random mutagenesis, in vivo mutagenesis, site directed mutagenesis, or the like. A nucleic acid encoding a parental enzyme typically includes a gene that, through the mechanisms of transcription and translation, produces an amino acid sequence corresponding to a parental enzyme, e.g., a native form of the enzyme. Modified enzymes also include chimeric enzymes that have identifiable component sequences (e.g., structural and/or functional domains, etc.) derived from two or more parents. Also included within the definition of modified enzymes are those comprising chemical modifications (e.g., attached substituent groups, altered substituent groups, etc.) relative to a reference sequence.

A "solid support" refers to a solid material which can be derivatized with, or otherwise attached to, a chemical moiety, such as a polynucleotide or the like. Exemplary solid supports include a plate, a bead, a microbead, a fiber, a whisker, a comb, a hybridization chip, a membrane, a single crystal, a ceramic layer, a a slide, a self-assembling monolayer, and the like.

"Cleavage" refers to a process of releasing a material or compound or moiety from another material or compound or moiety.

4.3 Detailed Description

It is to be understood that both the foregoing general description, including the drawings, and the following detailed description are exemplary and explanatory only and are not restrictive of this disclosure. In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

Disclosed herein are compositions and methods for sequencing polynucleotides, including single-molecule sequencing. The compositions disclosed herein include reversible terminator nucleotides that can be incorporated at the 3' terminus of a polynucleotide by a polymerase in a template dependent/directed manner. In some embodiments, the reversible terminator nucleotides generally include a hydroxyl group at the 3'-position of a sugar moiety, a blocking group at the 2'-position of the sugar moiety, and a label attached to the base. Upon incorporation of a reversible terminator nucleotide, the blocking group renders the polynucleotide non-extendible by the polymerase. In some embodiments, the incorporated reversible terminators also are generally resistant to 3'-5' exonucleases or "proofreading activities" of polymerases.

Following incorporation, the label of the reversible terminator nucleotide can detected to identify the base of the terminator nucleotide and therefore the corresponding base of the template polynucleotide. To permit a further round of extension, the polynucleotide can be treated with one or more reagents under conditions that remove the blocking group and the label. Therefore, the blocking group and the label can be removed under identical conditions. Upon removal of the label and blocking group, the 3' terminus of the polynucleotide can be further extended in a template dependent manner.

The structure of an exemplary reversible terminator nucleotide is shown in Formula I:

I in which $R_1$ represents H, OH, a hydrophilic group, or a hydrophobic group;

B represents a nucleobase comprising at least one homocyclic ring, at least one heterocyclic ring (with or without exocyclic heteroatoms), or at least one aryl group, or combinations thereof, BG represents a reversible blocking group;

Z represents O, $CH_2$, or S

---- represents a single or double bond.

In some embodiments, a reversible terminator nucleotide can include at least 1, 2, or 3 phosphate groups and/or phosphate analogs attached at the 5' position. In some embodiments, a reversible terminator nucleotide comprises a label. In some embodiments, $R_1$ and BG may be at the 2' and 3' positions, respectively.

Non-limiting examples of B groups of formula I include adenine, cytosine, guanine, thymine, uracil, 5-propynyl-uracil, 2-thio-5-propynyl-uracil, 5-methylcytosine, pseudo-isocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza- guanine), N8-(7-deaza-8-aza-adenine), isoC and isoG. Other non-limiting examples of suitable B groups include nucleobases disclosed in U.S. Pat. No. 5,432,272, 6,001,983, 6,037,120, 61,040,496, 6,357,163, 6,617,106, 6,977,161; U.S. Patent Publication Nos. 20040106108, 20050037398, 20060078936; EP1358352, EP1590482; and WO9220702, WO9220703, WO0233126 and WO04065550. Thus, the skilled artisan will appreciate that a B group of Formula I can be any naturally occurring or synthetic nucleobase that is suitable for hybridizing to a polynucleotide in a sequence-specific manner.

Blocking groups (BG) can be any moiety suitable for substantially inhibiting extension of a polynucleotide that comprises a 3' reversible terminator nucleotide of Formula I. The mechanism by which a BG inhibits extension can be by various methods, including but not limited to charge (e.g., positive or negative charge) or steric inhibition. In some embodiments, a BG can optionally render a polynucleotide substantially resistant to 3'-5' exonucleases and/or the "proof-reading activities" of polymerases. In addition to substantially inhibiting extension, the BG of Formula I are reversible. By "reversible" herein is meant that the BG can be substantially removed to yield a 3' terminus suitable for primer extension in a template directed manner. The removal of a BG can be accomplished using various methods and reagents, including but not limited to, an enzyme, such as an alkaline phosphatase.

In some embodiments, a BG can be $SO_3$.

In some embodiments, a BG can be $C(O)R_9$, wherein $R_9$ represents H, an alkyl group, a benzyl group, an aryl group, an alkenyl group, an alkynyl group, or combinations thereof In some embodiments, a BG can comprise the Formula II:

(II)

wherein where X represents O, S, $NR_3$, $CR_3R_4$, or $SiR_3R_4$;

Y represents $CR_5R_6R_7$, $SiR_5R_6R_7$, $OR_5$, $SR_5$, or $NHR_5$;

$R_2$ represents H, OH, $NHR_8$, $SR_8$, an alkyl group, a benzyl group, an aryl group, an alkenyl group, an alkynyl group, an alkoxy group, or combinations thereof; and $R_3$, $R_4$, $R_5$, $R_6$, $R_7$, and $R_8$ are independently selected from H, an alkyl group, a benzyl group, an aryl group, an alkenyl group, an alkynyl group, or combinations thereof.

In some embodiments, a BG can comprise the Formula III:

III wherein

X represents $CR_3R_4R_5$, $SiR_3R_4R_5$, $OR_3$, $SR_3$, or $NHR_3$;

$R_2$ represents H, $NHR_6$, $SR_6$, an alkyl group, a benzyl group, an aryl group, an alkenyl group, an alkynyl group, an alkoxy group, or combinations thereof; and $R_3$, $R_4$, $R_5$, and $R_6$ are independently selected from H, an alkyl group, a benzyl group, an aryl group, an alkenyl group, an alkynyl group, or combinations thereof.

In some embodiments, a BG can be a phosphate ($—PO_4$).

In some embodiments, a BG can be a $SO_3$.

In some embodiments, a BG can be $C(O)R$.

Methods of synthesizing the BG groups and their equivalents are known in the art.

The reversible terminators disclosed herein optionally comprise at least one label. In some embodiments, a label can be appended to the nucleobase (B) of a reversible terminator, for example, at homocyclic ring, a heterocyclic ring, or an aryl group (e.g., via C-5 of a pyrimidine, N-4 of cytidine, N-7 of a purine, N-6 of adenosine, C-8 of a purine, or another attachment site as in the art). In some embodiments, a label can be attached via an amide, an ester, a thioester, an ether, a thioether, a carbon-carbon, or other type of covalent bond. In some embodiments, a label can be attached to a sugar moiety (e.g., a ribose sugar) or an analog thereof of a reversible terminator nucleotide. In some embodiments, a label can be attached to a BG, such as, the BG of Formulas II and III or a phosphate, such as, by an amide, an ester, a thioester, an ether, a thioether, a carbon-carbon, or other bond. In some embodiments, a label can be appended to a reversible terminator nucleotide via a linker as described herein.

In various exemplary embodiments, a label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIG-DYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Other exemplary dyes are provided in Haugland, Molecular Probes Handbook of Fluorescent Probes and Research Products, Ninth Ed. (2003) and the updates thereto. Fluorescent dyes are generally readily available from various commercial suppliers including, e.g., Molecular Probes, Inc. (Eugene, Oreg.), Amersham Biosciences Corp. (Piscataway, N.J.), Applera Corp./Applied Biosystems Group (Foster City, Calif.). Other exemplay labels include, e.g., biotin, weakly fluorescent labels (Yin et al. (2003) Appl Environ Microbiol. 69(7):3938; Babendure et al. (2003) Anal. Biochem. 317(1):1; and Jankowiak et al. (2003) Chem Res Toxicol. 16(3):304), non-fluorescent labels, colorimetric labels, chemiluminescent labels (Wilson et al. (2003) Analyst. 128(5):480; Roda et al. (2003) Luminescence 18(2):72), Raman labels, electrochemical labels, bioluminescent labels (Kitayama et al. (2003) Photochem Photobiol. 77(3):333; Arakawa et al. (2003) Anal. Biochem. 314(2):206; and Maeda (2003) J. Pharm. Biomed. Anal. 30(6):1725), and an alpha-methyl-PEG labeling reagent as described in, e.g., U.S. Provisional Patent Application No. 60/428,484, filed on Nov. 22, 2002.

In some embodiments, a label comprises a radioisotope, such as $^3H$, $^{14}C$, $^{22}Na$, $^{32}P$, $^{33}P$, $^{35}S$, $^{42}K$, $^{45}Ca$, $^{59}Fe$, $^{125}I$, $^{203}Hg$, and the like. In some embodiments, a label can comprise at least one mass-modifying group, including but not limited to, deuterium, F, Cl, Br, I, S, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNY_2$, $CH_2CONY_2$, $(CH_2)_nOH$, $CH_2F$, $CHF_2$, $CF_3$, and a phosphorothioate group, where X is O, NH, NY, S, NHC(S), OCO(CH)$_n$COO, NHCO(CH$_2$)$_n$ COO, OSO$_2$2O, OCO(CH$_2$)$_n$, NHC(S)NH, OCO(CH$_2$)$_n$S, OCO(CH$_2$)S, NC$_4$O$_2$H$_2$S, OPO(O-alkyl), or OP(O-alkyl);

wherein n is an integer from 1 to 20 inclusive; and, Y is H, deuterium, an alkyl group, an alkoxy group, an aryl group, a polyoxymethylene group, a monoalkylated polyoxymethylene group, a polyethylene imine group, a polyamide group, a polyester group, a alkylated silyl group, a heterooligo, a polyaminoacid, a heterooligo/polyaminoacid group, or a polyethylene glycol group.

A large variety of linkers can be used to optionally link labels and BG to the reversible terminator nucleotides and will be apparent to one of skill in the art. A linker is generally of a structure that is sterically and electronically suitable for incorporation into a polynucleotide. In some embodiments, linkers can include an ether, a thioether, a carboxamide, a sulfonamide, a urea, a urethane, a hydrazine, or other moieties. In some embodiments, a linker can comprise from about 1 and to about 25 non-hydrogen atoms selected from, e.g., C, N, O, P, Si, S, etc., and comprise essentially any combination of exemplary groups, such as, an ether, a thioether, an amine, an ester, a carboxamide, a sulfonamide, hydrazide bonds, aromatic or heteroaromatic bonds. In some embodiments, a linker comprises a combination of single carbon-carbon bonds and carboxamide or thioether bonds. In some embodiments, longer linear segments of linkers can be utilized, the longest linear segment typically contains between about three to about 15 nonhydrogen atoms, including one or more heteroatoms.

Non-limiting examples of linker moieties include substituted (e.g., functionalized) or unsubstituted groups, such as imidazole/biotin linkers, polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine, etc.), and the like. (see, e.g., U.S. Pat. Nos. 4,711,958, 5,047,519, 5,175,269, 5,328,824, 6,339,392; and U.S. Patent Publication No. 20020151711. Additional examples of labeling and linkers are provided in Hermanson, Bioconjugate Techniques, Elsevier Science (1996).

In some embodiments, suitable linkers comprise photocleavable moieties, such as 2-nitrobenzyl moieties, alpha-substituted 2-nitrobenzyl moieties (e.g., 1-(2-nitrophenyl) ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Exemplary photocleavable linkers are described in U.S. Patent Publication No. 20030099972. In some embodiments, linkers include metals, such as platinum atoms. (see, e.g., U.S. Pat. No. 5,714,327). A number of linkers of varying lengths are commercially available from various suppliers including, e.g., Qiagen/Operon Technologies, Inc. (Alameda, Calif.), BD Biosciences Clontech (Palo Alto, Calif.), and Molecular BioSciences (Boulder, Colo.).

In some embodiments a suitable linker can be a fragmentable linker. By "fragmentable linker" as used herein refers to a linker that is capable of fragmenting in an electronic cascade self-elimination reaction. In various exemplary embodiments, fragmentation of the linker can result in the removal of a label and/or a BG from the reversible terminator nucleotides, disclosed herein. Examples of fragmentable linkers are disclosed in U.S. Patent Publication No. 20060003383.

In some embodiments, a fragmentable linker comprises a linker moiety and a trigger moiety. The linker moiety, the trigger moiety, and the optional label and/or BG can be connected to the linker moiety in any way that permits them to perform their respective functions. The trigger moiety comprises a substrate that can be cleaved or "activated" by a specified trigger agent. Activation of the trigger moiety initiates a spontaneous rearrangement that results in the fragmentation of the linker and release of the label and/or BG. In some embodiments, the release of the label and/or BG from the reversible terminator nucleotide may be caused by a ring closure mechanism. In some embodiments, a linker fragments via an elimination reaction. Various elimination reactions, including but not limited to, 1,4-, 1,6- and 1,8-elimination reactions have been used in the design of prodrugs and can be adapted for use in the compositions and methods described herein. (see, e.g., WO02083180, Gopin et al. Angew Chem int Ed. 32:327-332 (2003), Niculescu-Duvaz et al. J Med Chem. 41:5297-5309 (1998), Florent et al J Med Chem. 41:3572-3581 (1998), Niculescu-Duvaz et al. J Med Chem. 42:2485-2489 (1999), Greenwald et al. J Med Chem. 42:3657-3667 (1999), de Groot et al. Bioorg Med Chem Lett. 12:2371-2376 (2002), Ghosh et al. Tetrahedron Letters 41:4871-4874 (2000), Dubowchik et al. Bioconjugate Chem. 13:855-869 (2002), Michel et al. Atta-ur-Rahman (ed.) 21:157-180 (2000), Dinaut et al. Chem Commun. 1386-1387 (2001), Ohwada et al. Bioorg Med Chem Lett. 12:2775-2780 (2002), de Groot et al. J Org Chem. 66:8815-8830 (2001), Leu et al. J Med Chem. 42:3623-3628 (1999), Sauerbrei et al. Angew Chem Int Ed. 37:1143-1146 (1998), Veinberg et al. Bioorg Med Chem Lett. 14:1007-1010 (2004), Greenwald et al. Bioconjugate Chem. 14:395-403 (2003), and Lee et al Angew Chem Int Ed. 43:1675-1678 (2004).

Any means of activating the trigger moiety may be used, provided that the means used to activate the trigger moiety is capable of producing a detectable change, such as, a decrease in fluorescence and/or the removal of a BG and/or primer extension. Selection of a particular means of activation, and hence trigger moiety, may depend, in part, on the particular fragmentation reaction, as well as on other factors.

In some embodiments, activation is based upon cleavage of the trigger moiety. In these embodiments, the trigger moiety comprises a cleavage site that is cleavable by a chemical reagent or cleaving enzyme. In non-limiting exemplary embodiments, a trigger moiety can comprise a cleavage site that is cleavable by a sulfatase (e.g., $SO_3$ and analogs thereof), an esterase (e.g., $C(O)R_9$ and analogs thereof), or a phosphatase (e.g., $PO_4$ and analogs thereof. (Parent et al Current Opinion in Genetics & Development 1997; 7(3):386-391; Ellis et al. Applied & Environmental Microbiology 2002; 68(1):31-36; Bogaerts et al. Environmental Toxicology & Chemistry 1998; 17(8):1600-1605; Choudhury. Journal of Histochemistry and Cytochemistry 1972; 20(7):507-517). As a specific example, the trigger moiety can comprise a cleavage site that is cleavable by a phosphatase, such as, alkaline phosphatase.

The trigger moiety can further comprise additional residues and/or features that facilitate the specificity, affinity and/or kinetics of the cleaving enzyme. Depending upon the requirements of the particular cleaving enzyme, such cleaving enzyme "recognition moieties" can comprise the cleavage site or, alternatively, the cleavage site may be external to the recognition moiety.

The chemical composition of the trigger moiety will depend upon, among other factors, the requirements of the cleaving enzyme. For example, if the cleaving enzyme is a phosphatase, the trigger moiety can comprise a phosphate or a phosphate analog recognized and cleaved by the particular phosphatase. If the cleaving enzyme is a nuclease, the trigger moiety can comprise an oligonucleotide (or analog thereof) recognized and cleaved by a particular nuclease. If the cleaving enzyme is glycosidase, the trigger moiety can comprise a carbohydrate recognized and cleaved by a particular glycosidase (see, e.g., Florent et al. J Med Chem. 41:3572-3581 (1998), Ghosh et al. Tetrahedron Letters 41:4871-4874 (2000), Michel et al. Atta-ur-Rahman (ed.) 21:157-180 (2000), and Leu et al. J Med Chem. 42:3623-3628 (1999)). Exemplary structures recognized and cleaved by lipases and esterases, such as phosphatases, are also well known and include structures disclosed in Ohwada et al. Bioorg Med Chem Lett. 12:2775-2780 (2002), Sauerbrei et al. Angew Chem Int Ed. 37:1143-1146 (1998), Greenwald et al. J Med Chem Lett. 43:475-487 (2000), Dillon et al. Bioorg Med Chem Lett. 14:1653-1656 (1996), and Greenwald et al. J Med Chem. 47:726-734 (2004)). Exemplary structures recognized and cleaved by proteases/proteolytic enzymes are disclosed in Niculescu-Duvaz et al. J Med Chem. 41:5297-5309 (1998), Niculescu-Duvaz et al. J. Med Chem. 42:2485-2489 (1999), Greenwald et al. J Med Chem. 42:3657-36670 (1999), de Groot et al. Bioorg Med Chem Lett. 12:2371-2376 (2002), Dubowchik et al. Bioconjugate Chem. 13:855-869 (2002), and de Groot et al. J Org Chem. 66:8815-8830 (2001). Exemplary structures recognized and cleaved by catalytic antibodies are disclosed in Gopin et al. Angew Chem Int Ed. 42:327-332 (2003), Dinaut et al. Chem Commun. 1386-1387 (2001).

The linker moiety, the trigger moiety and the optional label and BG are connected to the linker moiety in any way that permits them to perform their respective functions. In some embodiments, the trigger moiety, label and/or BG are each, independently of the other, directly connected to the linker moiety. In other embodiments, the trigger moiety, label and/or BG can be, independently of the other, indirectly connected to the linker moiety via one or more optional linkages. The optional linkages can comprise a leaving group, which upon fragmentation of the substrate compound is released from the backbone of the linker, along with the moiety that is attached to it. For example, in some embodiments, the label can be attached to the backbone of the linker moiety via a linkage comprising a leaving group, while BG can be attached to the backbone of the linker moiety via a stable linkage, e.g., a linkage that does not dissociate from the backbone of the linker following the fragmentation reaction.

In some embodiments, the trigger moiety also serves as the linker moiety. In these embodiments, cleavage of the trigger moiety by a specified trigger agent also results in fragmentation of the linker and release of the label and/or BG.

In some embodiments, the trigger moiety also serves as the BG. In these embodiments cleavage of the trigger moiety by a specified trigger agent results in fragmentation of the linker and removal of the BG. Therefore, in these embodiments, linker fragmentation and removal of the BG can occur under identical conditions in a single step. As a result, a label attached to the fragmentable linker and the BG can be removed under identical conditions in a single step. An example of a trigger moiety that can also serve as a BG include but are not limited to a —$PO_4$, $SO_3$, and $C(O)R_9$.

Figure 1:
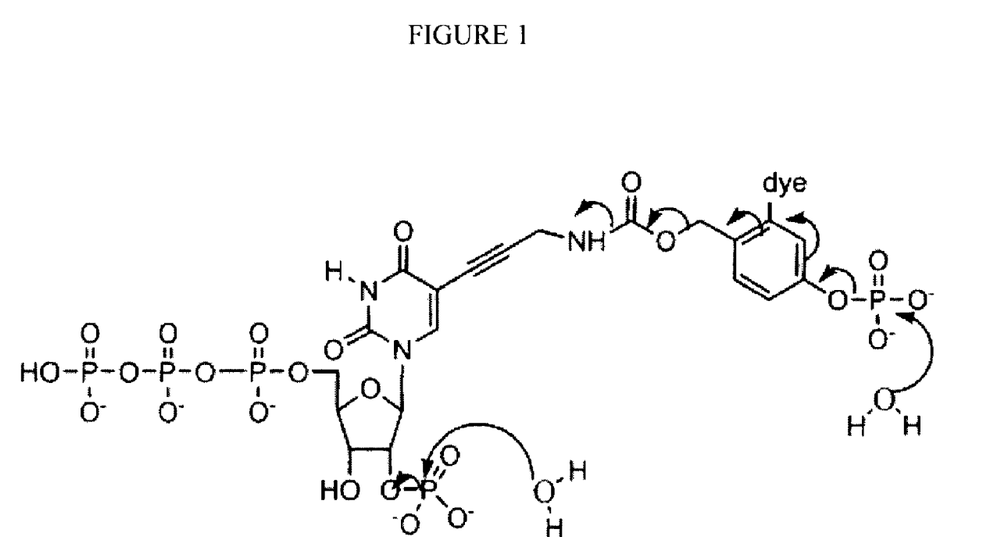
FIG. 1 provides the structure of an exemplary reversible terminator nucleotide comprising a dye label, a phosphate blocking group and a fragmentable linker comprising a phosphate trigger moiety.
Figure 2:
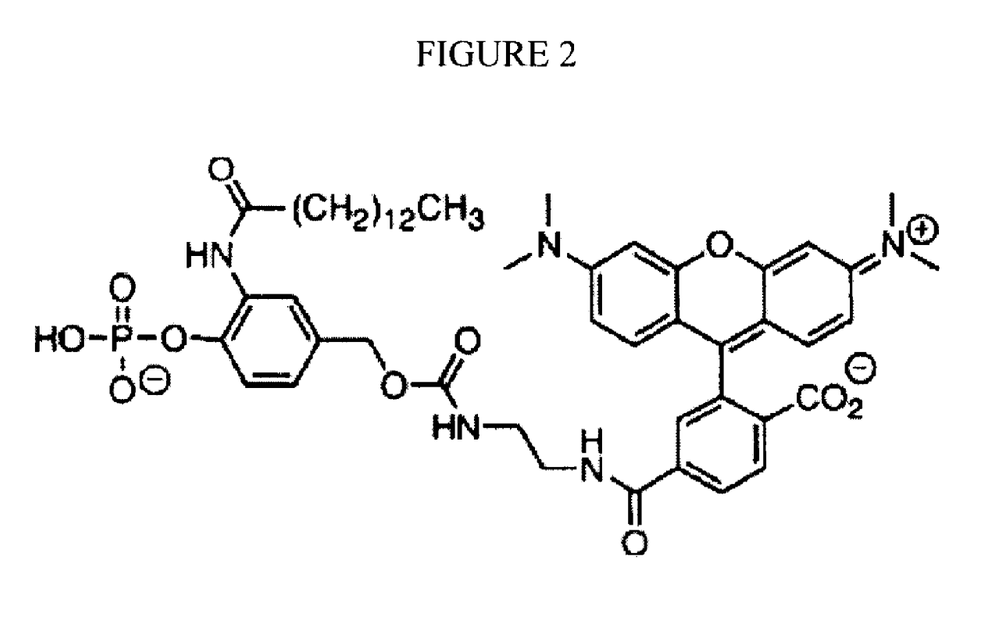
FIG. 2 provides an example of a fragmentable linker comprising a fluorescent label and a phosphate trigger moiety.
Figure 3:
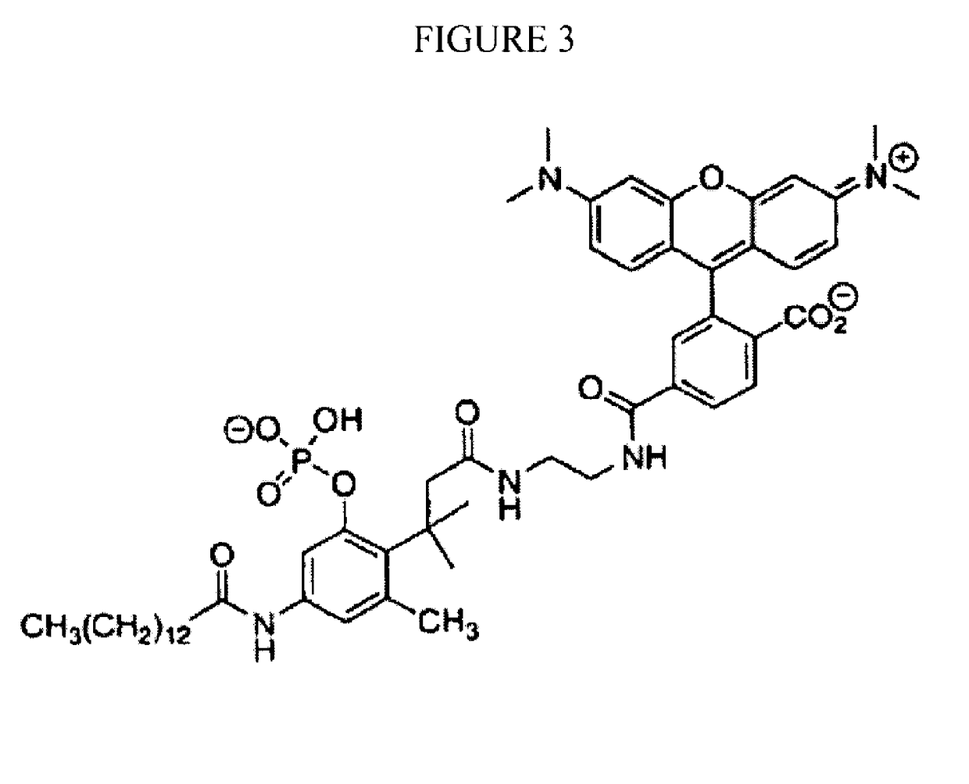
FIG. 3 provides an example of a fragmentable linker comprising a fluorescent label and a phosphate trigger moiety.

An example of a reversible terminator nucleotide comprising a phosphate BG and trigger moiety is shown in FIG. 1, in which a fragmentable linker is appended to a cytosine base. The phosphate on the fragmentable linker serves as the trigger moiety. Cleavage of the phosphate trigger moiety causes fragmentation of the linker and removal of the dye from the cytosine base. Cleavage of the phosphate BG at the 2' position of the ribose sugar permits the addition of an additional nucleotide at the 3' position. Other examples of fragmentable linkers comprising phosphate trigger moieties are shown in FIG. 2 and FIG. 3, in which the fragmentable linker comprises a fluorescent dyes. Methods of making these and other exemplary fragmentable linkers are disclosed in U.S. Patent Publication No. 20060003383.

In some embodiments, a phosphate BG and trigger moiety can be cleaved by an alkaline phosphatase ("ALP")(orthophosphate monoester phosphohydrolases [alkaline optimum]; (EC 3.1.3.1). In general, ALPs are homodimeric non-specific metalloenzymes that catalyze phosphomonoesterase reactions. (Coleman. Annu Rev Biophys Biomol Struct. 1992;21:441-483; Holtz et al. FEBS Lett. 1999;462:7-1 1; Holtz et al. J Biol Chem. 1999; 274:8351-8354; Kim et al. Clin Chim Acta 1989; 186;175-188; Manes et al. Genomics 1990; 8:541-554; McComb et al. Alkaline Phosphatase 1979 Plenum Press, NY; Trowsdale et al. Biochem Soc Trans. 1990; 18:178-180). The reaction conditions for ALPS are well-known in the art and non-limiting examples of ALPs suitable for use in the disclosed methods include shrimp alkaline phosphatase (de Backer et al. J Mol Biol. 2002 May 17; 318(5):1265-74; Olsen et al. Comp Biochem Physiol. 1991 99B:755-61), bovine intestinal alkaline phosphatase (Weissig et al. Biochem J. 1993; 290:503-508), and ALPs isolated from *Pyrococcus abyssi* (Erauso et al. Arch Microbiol. 1993; 160:338-349; Zappa et al. Appl Environ Microbiol. 2001 October; 67(10):4504-11), *Pyrococcus horikoshii* sp. (Gonzalez et al Extremophiles 1998;2:123-130), *Thermatoga neopolitana* (Dong et al. Enzyme Microb Technol. 1997; 21:335-340), *Thermus caldophilus* GK24 (Park et al. FEMS Microbiol Lett. 1999; 180:133-139), *Thermus thermophilus* (Pantazaki et al. Appl. Biochem Biotechnol. 1998; 75:249-259), *Haloarcula* (Goldman et al J Bacteriol. 1990; 172:7065-7070), *Halobacterium* (Bonet et al. Biochem Mol Biol Int. 1994; 34:1109-1120; Fitt et al. Biochem J. 1979; 181:347-353), *Prevotello intermedia* (Ansai et al. FEBS Lett. 1998; 428:157-160), *Bacillus* (Hulett. Mol Microbiol. 1996; 19:933-939; Mori et al. Biotechnol Appl Biochem 1999; 29:235-239; Sharipova et al. Biochem. (Moscow) 1998;63: 1178-1182; Sharipova et al. Biochem Mol Biol Int. 1996; 38:753-761; Spencer et al. J Bacteriol. 1981; 145:926-933), *Vibrio* (Hauksson et al Enzyme Microb Technol. 2000; 27:66-73), *Escherichia coli* (Coleman. Annu Rev Biophys Biomol Struct. 1992; 21:441-83; Derman et al J Bacteriol. December 1991; 173(23):7719-22; Hulett et al. J Biol Chem. 1991; 266:1077-1084; Janeway et al. Biochemistry 1993; 32:1601-1609; Kane. Curr Opin Biotechnol. 1995; 6:494-500; Karamyshev et al. J Mol Biol. Apr. 10, 1998; 277(4):859-70; Kim et al. Biotechnol Lett. 1998; 20:207-210; Murphy et al. J Mol Biol. 1995; 253:604-617; Murphy et al. J Biol Chem. 1993; 268:21497-21500), *Bacteroides* (Yamashita et al. Infect Immun. 1990; 58:2882-2887), *Gadus morhua* (Asgeirsson et al. Comp Biochem Physiol. 1995; 110B:315-329), *Scylla serrata* (J Biochem Cell Biol. 2000;32:879-885), humans (Berget et al. PNAS USA 1987;84:695-698; Weiss et al PNAS USA 1986;83:7182-7186), insects (Eguchi. Comp Biochem Physiol. 1995; 111B: 151-162), *Neurospora* (Morales et al. Braz J Med Biol Res. 2000; 33:905-912), Antarctic strain TAB5 (Rina et al. Eur J Biochem 2000; 267:1230-1238).

The reversible terminator nucleotides can be employed in virtually any method of analyzing or detecting a polynucleotide. In various non-limiting examples, suitable polynucleotide may be single or double-stranded, or a combination thereof, linear or circular, a chromosome or a gene or a portion or fragment thereof, a regulatory polynucleotide, a restriction fragment from, for example, a plasmid or chromosomal DNA, genomic DNA, mitochondrial DNA, DNA from a construct or library of constructs (e.g., from a YAC, BAC or PAC library), RNA (e.g., mRNA, rRNA or vRNA) or a cDNA or a cDNA library. As known in the art, a cDNA is a single- or double-stranded DNA produced by reverse transcription of an RNA template. Therefore, some embodiments include a reverse transcriptase and one or more primers suitable for reverse transcribing an RNA template into a cDNA. Reactions, reagents and conditions for carrying out such "RT" reactions are known in the art (see, e.g., Blain et al, 1993, *J. Biol. Chem.* 5:23585-23592; Blain et al., 1995, *J. Virol.* 69:4440-4452; *PCR Essential Techniques* 61-63, 80-81, (Burke, ed., J. Wiley & Sons 1996); Gubler et al., 1983, *Gene* 25:263-269; Gubler, 1987, *Methods Enzymol.,* 152:330-335; Sellner et al., 1994, *J. Virol. Method.* 49:47-58; Okayama et al., 1982, *Mol. Cell. Biol.* 2:161-170; and U.S. Pat. Nos. 5,310,652, 5,322,770, 6,300,073, these disclosures of which are incorporated herein by reference. In some embodiments, a polynucleotide may include a single polynucleotide (e.g., a chromosome, plasmid) from which one or more different sequences of interest may clonally amplified and analyzed. Methods of clonal amplification are disclosed in *U.S. application Ser. No. 11/377,763.

In some embodiments, polynucleotides can be analyzed in a parallel manner. For example, discrete or isolated polynucleotides can be analyzed in parallel as a result of their attachment to a discrete area of a surface or isolation in a well of a multi-well plate. Therefore, in some embodiments, at least at least 100, 500, 1000, 10000, 50000, 100000, 300000, 500000, or 1000000 polynucleotides can be analyzed in parallel. Generally, parallel reactions produce discrete detectable signals that can be associated or linked to individual polynucleotides.

In some embodiments, polynucleotides can be sequenced using the reversible terminator nucleotides based on sequencing-by-synthesis techniques. The sequencing-by-synthesis technique employs controlled synthesis of nucleic acids (e.g., primer extension) and the detection of each incorporated reversible terminator nucleotide in a step-by-step manner. For example, in some embodiments, a primer can be hybridized to a polynucleotide that is immobilized to surface in the presence of four reversible terminator nucleotide triphosphates each labeled with a spectrally resolvable fluorescent dye and a polymerase. The incorporation of a first reversible terminator at the 3' terminus of the sequencing primer prevents further extension. To detect the incorporated reversible terminator, the unincorporated reversible terminators are washed away and the incorporated reversible terminator is detected by its fluorescent label. To permit a further cycle of extension and detection, the label and BG are removed from the incorporated reversible terminator. In embodiments, that employ a phosphate BG and a fragmentable linker comprising a phosphate trigger moiety to a reversible terminator, the BG and label can be removed under identical conditions using an alkaline phosphatase, such as shrimp alkaline phosphatase, as described above. Therefore, an enzymatic reaction to can be employed to efficiency remove the label and BG under identical conditions. Following removal of the label and BG from the incorporated reversible termiantor, the alkaline phosphatase can be inactivated or washed away prior to the reintroduction of the four reversible terminator nucleotide triphosphates and polymerase. For example, in some embodiments, shrimp alkaline phosphatase can be inactivated by incubation at 65° C. for 15 min.

In practicing the disclosed methods, many conventional techniques in molecular biology and recombinant DNA can be used. These techniques are well known in the art and disclosed in, for example, Current Protocols in Molecular Biology, Volumes I, II, and III, 1997 (F. M. Ausubel ed.); Sambrook et al., 2001, Molecular Cloning: A Laboratory Manual, Third Edition, Cold Spring Harbor Laboratory Press, Cold Spring Harbor, N.Y.; Berger and Kimmel, Guide to Molecular Cloning Techniques, Methods in Enzymology volume 152 Academic Press, Inc., San Diego, Calif. (Berger); DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

Methods of attaching a polynucleotide to either covalently or non-covalently to a solid support or a surface are also known in the art. Solid supports can comprise various materials, including but not limited to any one or more of plastic, glass, ceramic, metal, resin, gel and a membrane. Exemplary types of solid supports include but are not limited plates, slides, beads, microbeads, whiskers, fibers, combs, hybridization chips, membranes, single crystals, ceramics, and self-assembling monolayers.

Polynucleotides can be attached to a solid support by covalent binding such as by conjugation with a coupling agent or by non-covalent binding such as electrostatic interactions, hydrogen bonds or antibody-antigen coupling, or by combinations thereof. Exemplary coupling agents include biotin/avidin, biotin/streptavidin, *Staphylococcus aureus* protein A/IgG antibody $F_c$ fragment, and streptavidin/protein A chimeras (Sano et al. (1991) Bio/Technology 9:1378, which is incorporated by reference), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids. In some embodiments, polynucleotides can be attached to solid supports via spacer moieties between the nucleic acids and the solid support.

In some embodiments, a polynucleotide can be attached to a solid support via a cleavable attachment. Cleavable attachments can be created by attaching cleavable chemical moieties between the polynucleotides and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds which can be cleaved by proteases and phosphodiester bonds which can be cleaved by nucleases.

Chemical agents such as β-mercaptoethanol, dithiothreitol (DTT) and other reducing agents cleave disulfide bonds. Other agents that may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

A variety of nucleic acid polymerases may be used in the sequencing and other methods described herein. In various exemplary embodiments, a polymerase can be a thermostable polymerase or a thermally degradable polymerase. Suitable thermostable polymerases include, but are not limited to, polymerases isolated from *Thermus antranikianii*, *Thermus aquaticus*, *Thermus caldophilus*, *Thermus chliarophilus*, *Thermusfiliformis*, *Thermusfiavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Anaerocellum thermophilum*, *Bacillus caldotenax*, *Bacillus stearothermophilus*, *Pyrococcus woesei*, *Pyrococcusfuriosus*, and *Thermococcus litoralis*. For example, the polymerase optionally lacks an F to Y mutation in helix O of the enzyme or otherwise lacks a mutation that enhances incorporation of 3'-deoxynucleotides by the enzyme. In some embodiments, a polymerase comprises a 3'-5'exonuclease activity. In some embodiments, a polymerase can be thermodegradable, such as, *E. coli* DNA polymerase I, the Klenow fragment of *E. coli* DNA polymerase I, T4 DNA polymerase, T5 DNA polymerase, T7 DNA polymerase, and others.

Non-limiting examples of commercially available polymerases that suitable for the methods described herein include, but are not limited to, TaqFS®, AmpliTaq CS (Perkin-Elmer), AmpliTaq FS (Perkin-Elmer), Kentaq1 (AB Peptide, St. Louis, Mo.), Taquenase (ScienTech Corp., St. Louis, Mo.), ThermoSequenase (Amersham), Bst polymerase, Vent$_R$(exo⁻) DNA polymerase, Reader™ Taq DNA polymerase, VENT™ DNA polymerase (New England Biolabs), DEEP-VENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

In some embodiments, a polymerase can be modified, which can enhance the incorporation of the reversible terminator nucleotides disclosed herein. Exemplary modified polymerases are disclosed in U.S. Pat. Nos. 4,889,818, 5,374,553, 5,420,029, 5,455,170, 5,466,591, 5,618,711, 5,624,833, 5,674,738, 5,789,224, 5,795,762, 5,939,292; and U.S. Patent Publication Nos. 20020012970, 20040005599. A non-limiting example of a modified polymerase includes G46E E678G CS5 DNA polymerase, G46E E678G CS5 DNA polymerase, E615G Taq DNA polymerase, ΔZO5R polymerase, and G46E L329A E678G CS5 DNA polymerase disclosed in U.S. Patent Publication No. 20050037398. The production of modified polymerases can be accomplished using many conventional techniques in molecular biology and recombinant DNA described herein and known in the art. In some embodiments, wherein the 2'-phosphate unblocking generates a 2'-hydroxyl, i.e., a ribonucleotide, polymerase mutants, such as those described in U.S. Patent No. 5,939,292, which incorporate NTPs as well as dNTPs can be used.

The products of methods disclosed herein can be analyzed by a wide variety of methods which can be selected at the discretion of the practitioner. Analytical methods include but are not limited to gel electrophoresis, capillary electrophoresis (CE: e.g., 3730 DNA Analyzer, 3730×1 DNA Analyzer, 3100-Avant genetic analyser, and 270A-HT Capillary Electrophoresis system (Applied Biosystems, Foster City, Calif.)) (see, e.g., U.S. Pat. Nos. RE37941, 5,384,024, 6,372,106, 6,372,484, 6,387,234, 6,387,236, 6,402,918, 6,402,919, 6,432,651, 6,462,816, 6,475,361, 6,476,118, 6,485,626, 6,531,041, 6,544,396, 6,576,105, 6,592,733, 6,596,140, 6,613,212, 6,635,164, and 6,706,162) using various polymers (e.g., separation polymer (e.g., POP-4™ POP-6™, or POP-7™ (Applied Biosystems, Foster City, Calif.), linear polyacrylamide (LPA: Kleparnik et al., 2001, *Electrophoresis* 22(4):783-8; Kotler et al., 2002, *Electrophoresis* 23(17):3062-70; Manabe et al, 1998, *Electrophoresis* 19:2308-2316)), chromatography, thin layer chromatography, or paper chromatography, by laser-induced fluorescence (see, e.g., U.S. Pat. Nos. 5,94,5526, 5,863,727, 5,821,058, 5,800,996, 5,332,666, 5,633,129, and 6,395,486), autoradiagraphy, chemiluminescence, mass spectrometric methods (see, e.g., U.S. Pat. Nos. 6,225,450 and 510,412), microcapillary electrophoretic methods (see, e.g., Doherty et al., 2004, *Analytical Chemistry* 76:5249-5256; Ertl et al., 2004, *Analytical Chemistry* 76:3749-3755; Haab et al., 1999, *Analytical Chemistry* 71:5137-5145 (1999); Kheterpal et al., 1999, *Analytical Chemistry* 71:31A-37A; Lagally et al., 2000, *Sensors and Actuators* B 63:138-146; Lagally et al., 2001, *Anal. Chem.* 73:565-570; Lagally et al., 2003, *Genetic Analysis Using a Portable PCR-CE Microsystem*, in *Micro Total Analysis Systems* Vol. 2, Northrup et al. (eds.) pp. 1283-1286; Liu et al., 1999, *Anal. Chem.* 71:566-573; Medintz et al., 2000, *Electrophoresis* 21:2352-2358; Medintz et al., 2001, *Genome Research* 11:413-421; Paegel et al., *Current Opinions in Biotechnology* 14:42-50; Scherer et al., 1999, *Electrophoresis* 20:1508-1517; Shi et al., 1999, *Analytical Chemistry* 71:5354-5361; Wedemayer et al., 2001, *BioTechniques* 30:122-128; U.S. Pat. Nos. 6,787,015, 6,787,016; U.S. Application Nos. 20020166768, 20020192719, 20020029968, 20030036080, 20030087300, 20030104466, 20040045827, 20040096960; EP1305615; and WO 02/08744).

In some embodiments, the detectable signals generated by the labels disclosed herein can be detected using photomultiplier tubes (PMTs), charge-coupled devices (CCDs), intensified CCDs, photodiodes, avalanche photodiodes, optical sensors, scanning detectors, or the like. Detectors such as these are readily available from various commercial sources including, e.g., Applied Biosystems (Foster City, Calif.). Detection systems of use in practicing the methods of the invention are described further in, e.g., Skoog et al., Principles of Instrumental Analysis, 5th Ed., Harcourt Brace College Publishers (1998) and Currell, Analytical Instrumentation: Performance Characteristics and Quality, John Wiley & Sons, Inc. (2000).

The primers (e.g., sequencing primers) employed in the methods disclosed herein, generally, should be sufficiently long to prime template-directed synthesis under the conditions of the reaction. The exact lengths of the primers may depend on many factors, including but not limited to, the desired hybridization temperature between the primers and polynucleotides, the complexity of the different target polynucleotide sequences, the salt concentration, ionic strength, pH and other buffer conditions, and the sequences of the primers and polynucleotides. The ability to select lengths and sequences of primers suitable for particular applications is within the capabilities of ordinarily skilled artisans (see, e.g., Sambrook et al. *Molecular Cloning: A Laboratory Manual* 9.50-9.51, 11.46, 11.50 (2d. ed., Cold Spring Harbor Laboratory Press); Sambrook et al., *Molecular Cloning: A Laboratory Manual* 10.1-10.10 (3d. ed. Cold Spring Harbor Laboratory Press)). In some embodiments, the primers contain from about 15 to about 35 nucleotides that are suitable for hybridizing to a target polynucleotide and form a substrate suitable for DNA synthesis, although the primers may contain more or fewer nucleotides. Shorter primers generally require lower temperatures to form sufficiently stable hybrid complexes with target sequences. The capability of polynucleotides to anneal can be determined by the melting temperature ("$T_m$") of the hybrid complex. $T_m$ is the temperature at which 50% of a polynucleotide strand and its perfect complement form a double-stranded polynucleotide. Therefore, the $T_m$ for a selected polynucleotide varies with factors that influence or affect hybridization. In some embodiments, in which thermocycling occurs, the primers can be designed to have a melting temperature ("$T_m$") in the range of about 60-75° C. Melting temperatures in this range tend to insure that the primers remain annealed or hybridized to the target polynucleotide at the initiation of primer extension. The actual temperature used for a primer extension reaction may depend upon, among other factors, for example, the concentration of the primers. For reactions carried out with a thermostable polymerase such as Taq DNA polymerase, in exemplary embodiments primers can be designed to have a $T_m$ in the range of about 60 to about 78° C. or from about 55 to about 70° C. The melting temperatures of the different primers can be different; however, in an alternative embodiment they should all be approximately the same, i.e., the $T_m$ of each primer, for example, in a parallel reaction can be within a range of about 5° C. or less. The $T_m$s of various primers can be determined empirically utilizing melting techniques that are well-known in the art (see, e.g., Sambrook et al *Molecular Cloning: A Laboratory Manual* 11.55-11.57 (2d. ed., Cold Spring Harbor Laboratory Press)). Alternatively, the $T_m$ of a primer can be calculated. Numerous references and aids for calculating $T_m$s of primers are available in the art and include, by way of example and not limitation, Baldino et al. *Methods Enzymology.* 168:761-777; Bolton et al., 1962, *Proc. Natl. Acad. Sci.* USA 48:1390; Bresslauer et al., 1986, *Proc. Natl. Acad. Sci.* USA 83:8893-8897; Freier et al., 1986, *Proc. Natl. Acad. Sci.* USA 83:9373-9377; Kierzek et al, *Biochemistry* 25:7840-7846; Montpetit et al., 1992, *J. Virol. Methods* 36:119-128; Osborne, 1991, *CABIOS* 8:83; Rychlik et al., 1990, *Nucleic Acids Res.* 18:6409-6412 (*erratum,* 1991, Nucleic Acids Res. 19:698); Rychlik. *J. NIH Res.* 6:78; Sambrook et al. *Molecular Cloning: A Laboratory Manual* 9.50-9.51, 11.46-11.49 (2d. ed., Cold Spring Harbor Laboratory Press); Sambrook et al., *Molecular Cloning: A Laboratory Manual* 10.1-10.10 (3d. ed. Cold Spring Harbor Laboratory Press)); SantaLucia, 1998, *Proc. Natl. Acad. Sci.* USA 95:1460-1465; Suggs et al, 1981, In *Developmental Biology Using Purified Genes* (Brown et al., eds.), pp. 683-693, Academic Press; Wetmur, 1991, *Crit. Rev. Biochem. Mol. Biol.* 26:227-259, which disclosures are incorporated by reference. Any of these methods can be used to determine a $T_m$ of a primer.

As the skilled artisan will appreciate, in general, the relative stability and therefore, the $T_m$s, of RNA:RNA, RNA:DNA, and DNA:DNA hybrids having identical sequences for each strand may differ. In general, RNA:RNA hybrids are the most stable (highest relative $T_m$) and DNA:DNA hybrids are the least stable (lowest relative $T_m$). Accordingly, in some embodiments, another factor to consider, in addition to those described above, when designing a primer is the structure of the primer and target polynucleotide. For example, in the embodiment in which an RNA polynucleotide is reverse transcribed to produce a cDNA, the determination of the suitability of a DNA primer for the reverse transcription reaction should include the effect of the RNA polynucleotide on the $T_m$ of the primer. Although the $T_m$s of various hybrids may be determined empirically, as described above, examples of methods of calculating the $T_m$ of various hybrids are found at Sambrook et al. *Molecular Cloning: A Laboratory Manual* 9.51 (2d. ed., Cold Spring Harbor Laboratory Press).

The sequences of primers useful for the disclosed methods are designed to be substantially complementary to regions of the target polynucleotides. By "substantially complementary" herein is meant that the sequences of the primers include enough complementarity to hybridize to the target polynucleotides at the concentration and under the temperature and conditions employed in the reaction and to be extended by the DNA polymerase.

The compositions and reagents described herein can be packaged into kits. In some embodiments, a kit comprises one or more reversible terminator nucleotides. In some embodiments, each reversible nucleotide can comprise a label (e.g., a fluorescent dye, a radioisotope, a mass-modifying group etc.). In some embodiments, a label can be attached to a reversible terminator nucleotide by a fragmentable linker. In some embodiments, the BG of a reversible terminator nucleotide and the trigger moiety can be removed under identical conditions by the action of an enzyme, such as, an alkaline phosphatase. Therefore, in some embodiments, a kit can include a trigger agent suitable for activating a trigger moiety and removing the BG from a reversible terminator nucleotides. In some embodiments, a kit can comprise a polymerase, including but not limited to, a modified polymerase as described herein. In some embodiments, a kit can comprise one or more sequencing primers. In some embodiments, a kit can further include a template polynucleotide suitable for sequencing which can optionally be attached to a surface or solid support. In some embodiments, a kit can comprise one or more reaction compartments comprising reagents suitable for performing a reaction, such as a sequencing reaction, selected at the discretion of a practitioner. For example, in some embodiments, a kit can comprise one or more reaction compartments comprising one more sequencing reagents. In some embodiments, a component of a kit can be used in conjunction with one or more reagents from commercially available kits, including, but not limited to, those available from Applied Biosystems (i.e., Big Dye® Terminator Cycle Sequencing Kit), Epicentre (i.e., SequiTherm™ Cycle Sequencing Kit), Amersham (i.e., DYEnamic Direct Dye-Primer Cycle Sequencing Kits), Boehringer Mannheim (i.e., CycleReader™ DNA Sequencing Kit), Bionexus Inc. (i.e., AccuPower DNA Sequencing Kit), and USB cycle sequencing kits (i.e., Thermo Sequenase™ Cycle Sequencing Kit).

The various components included in the kit are typically contained in separate containers, however, in some embodiments, one or more of the components can be present in the same container. Additionally, kits can comprise any combination of the compositions and reagents described herein. In some embodiments, kits can comprise additional reagents that may be necessary or optional for performing the disclosed methods. Such reagents include, but are not limited to, buffers, molecular size standards, control polynucleotides, and the like.

In this application, the use of the singular includes the plural unless specifically stated otherwise. The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments have been illustrated and described, it will be appreciated that various changes can be made without departing from the spirit and scope of the invention(s).

What is claimed is:

1. A nucleoside comprising a base and a sugar in which a phosphate moiety label is attached to said base and a phosphate moiety protecting group is attached to said sugar, wherein said phosphate moiety label and said phosphate moiety protecting group are detachable from said nucleoside by an enzyme.

2. A nucleoside comprising a base and a sugar in which a $SO_3$ moiety label is attached to said base and a $SO_3$ moiety protecting group is attached to said sugar, wherein said $SO_3$ moiety label and said $SO_3$ moiety protecting group are detachable from said nucleoside by an enzyme.

3. A nucleotide comprising a base and a sugar in which a phosphate moiety label is attached to said base and a phosphate moiety protecting group is attached to said sugar, wherein said phosphate moiety label and said phosphate moiety protecting group are detachable from said nucleotide by an enzyme.

4. A nucleotide comprising a base and a sugar in which a $SO_3$ moiety label is attached to said base and a $SO_3$ moiety protecting group is attached to said sugar, wherein said $SO_3$ moiety label and said $SO_3$ moiety protecting group are detachable from said nucleotide by an enzyme.

5. A nucleotide comprising a base and a sugar in which a label is attached to said base and a protecting group is attached to said sugar, wherein said label and said protecting group are detachable from said nucleotide by a phosphatase enzyme.

6. A nucleotide comprising a base and a sugar in which a label is attached to said base and a protecting group is attached to said sugar, wherein said label and said protecting group are detachable from said nucleotide by a shrimp alkaline phosphatase enzyme.

* * * * *